United States Patent [19]

Reed

[11] Patent Number: 4,506,012

[45] Date of Patent: Mar. 19, 1985

[54] PRODUCTION OF ORGANIC ACIDS BY A CONTINUOUS FERMENTATION PROCESS

[75] Inventor: William M. Reed, Bloomingdale, Ill.

[73] Assignee: CPC International Inc., Englewood Cliffs, N.J.

[21] Appl. No.: 474,412

[22] Filed: Mar. 11, 1983

[51] Int. Cl.$^3$ .......................... C12P 7/56; C12P 7/40; C12N 11/14
[52] U.S. Cl. .................................. 435/139; 435/136; 435/140; 435/176; 435/177; 435/178; 435/179
[58] Field of Search .............. 435/136, 139, 140, 176, 435/177, 178, 179

[56] References Cited

U.S. PATENT DOCUMENTS

| | | | |
|---|---|---|---|
| 4,204,041 | 5/1980 | Bailey et al. | 435/177 |
| 4,371,619 | 2/1983 | Schwartz et al. | 435/140 |
| 4,438,196 | 3/1984 | Lantero | 435/177 |

*Primary Examiner*—Sam Rosen
*Attorney, Agent, or Firm*—Stanley M. Parmerter

[57] ABSTRACT

An improved process for preparing organic acids by a continuous homoacidogenic fermentation is disclosed. This process provides increased volumetric productivity of the acid by employing a microorganism growing on the surface of a support material such as activated carbon or corn cob granules.

12 Claims, No Drawings

4,506,012

PRODUCTION OF ORGANIC ACIDS BY A CONTINUOUS FERMENTATION PROCESS

FIELD OF THE INVENTION

This invention relates to a method for the production of organic acids by a continuous fermentation process.

BACKGROUND OF THE INVENTION

The production of organic chemicals by microorganisms is well known to those familiar with the fermentation art. Such fermentation reactions frequently produce a variety of products in dilute aqueous solutions. The expense of separating the chemicals from each other and from the large volumes of water has been so great that production of chemicals by fermentation has not been able to compete with production of the same chemicals from fossil fuel sources. However, the gradual depletion of petroleum fossil fuel with the resultant increase in prices of petrochemical feedstocks has revived interest in such fermentation reactions which can convert carbohydrates that are renewable raw materials into simple organic chemicals.

Homoacidogenic fermentation reactions are of particular interest because they produce a single acidic compound in the fermentation. Products which can be obtained by these fermentations include the industrially important acetic and lactic acids. The fermentation of glucose by *Clostridium thermoaceticum* (hereinafter written *C. thermoaceticum*) is especially attractive since it can produce theoretically 3 moles of acetate from 1 mole of glucose.

Studies of these fermentation reactions have been reviewed by Zeikus, J. G., *Ann. Rev. Microbiol.*, 34, 423–464 (1980). He has classified the microorganisms useful for carrying out chemical-producing fermentations. These have been divided into three classes: the acidogens, the solventogens and the methanogens, which produce acids, solvents and methane respectively. Among the acidogens, the homoacid-forming species that produce either acetic, lactic, or butyric acid are described as being the most interesting in terms of product yeilds.

It would be of considerable commercial interest, therefore, if a process could be developed for the production of acids using these fermentation reactions in a continuous mode. In a recent disclosure, Wang, G. Y. and Wang, D. I. C., 178 National A.C.S. Meeting, Las Vegas, Nev., August, 1980, a method for immobilizing the thermophilic anaerobic homoacidogenic bacterium, *C. thermoaceticum*, in agar and carrageenan gel was described. To test the stability of this gel for continuous acetic acid production, a repeated batch experiment was performed using the gel. Acetic acid productivity at the rate of 2.2 grams per liter-hour (g/l-hour) was achieved. Although this is a distinct improvement over the 0.5 g/l-hr produced by the cells in a batch fermentation, it is still unacceptably low.

In order for a continuous fermentation process to be acceptable for commercial use, it must be operated at a high dilution rate. Dilution rate is a value obtained by dividing the flow rate of the fermentation medium through the reactor by the volume of the reactor. Furthermore, the volumetric productivity, i.e., the amount of product formed per unit volume of reactor in a given time, must be high when the fermentation is carried out at a high dilution rate. A continuous fermentation process has now been discovered which can be carried out at a high dilution rate and which gives a volumetric productivity much greater than that of the best process previously disclosed.

SUMMARY OF THE INVENTION

In accordance with the present invention, there is provided a process for the continuous production of an organic acid by a homoacidogenic fermentation reaction characterized in that the acid is produced by fermenting a carbohydrate solution by passing the solution over cells of a homoacidogenic microorganism growing on the surface of a support material selected from the group consisting of activated carbon or corn cob granules under conditions of pH, temperature and dilution rate effective to produce the acid at a volumetric productivity of at least about 5 g/l-hr.

DETAILED DESCRIPTION OF THE INVENTION

The process of this invention is suitable for the preparation of organic acids produced by homoacidogenic fermentation reactions. A single acid is the only organic product of such fermentations. This contrasts with the other acidogenic and solventogenic fermentations which produce more than one organic compound.

Any microorganism which ferments carbohydrates to give one acid as the principal product is suitable for use in the practice of this invention. Examples of suitable organisms are *Clostridium formicoaceticum, Acetobacterium woodii, Lactobacillus casei, Clostridium thermoautotrophicum, Acetogenium kivui* and *Lactobacillus delbrueckii*. A particularly suitable organism is *C. thermoaceticum* which is capable of converting glucose to acetic acid in nearly quantitative yields.

The fermentation process of this invention is carried out in a fermentation medium which comprises an aqueous solution containing dissolved carbohydrates, nutrients and growth factors needed for growth of the microorganism. The medium is sterilized before use by heat or other means well known in the art.

The carbohydrate used in the practice of this invention can be any carbohydrate that is converted to the desired acid by the microorganism used. For most microorganisms, glucose is a convenient carbohydrate. In the case of *C. thermoaceticum*, the fermentation can also be carried out with fructose or xylose instead of glucose.

Small concentrations of metal ions and other growth factors required by the particular microorganism used are added to the fermentation medium. Furthermore, the pH of the medium is maintained in a range suitable for the growth of the microorganism. This can be accomplished by the addition of buffer salts to the medium.

The process of this invention is carried out by means of a continuous fermentation using cells of a microorganism that are growing on the surface of a solid support held in a reactor. The support can be any inert material which has good adsorptive capacity for the cells and allows adequate flow of the medium through the reactor. Materials such as activated carbon, pumice stone and corn cob granules can be used.

Any activated carbon which shows good adsorptive capacity for the cells and allows adequate flow of the fermentation medium through the reactor is suitable for the process of this invention. CPG Pittsburgh activated carbon, available from the Calgon Corporation, Pittsburgh, Pa., is an example of such a suitable carbon.

Corn cob granules of about 14 to 20 mesh (U.S. Standard Screen sizes with sieve openings of 1.41 mm to 0.84 mm), or larger, also furnish suitable support for fixed-cell fermentations and permit desired flow of the medium. Productivity using the corn cob granules as a support was as good as that using activated carbon as a support and far superior to the productivity using other supports. Since corn cob granules are much less expensive than activated carbon, they offer an important advantage when large amounts of support material are needed. Furthermore, spent corn cob granules are suitable as animal feed. This provides an economical way to dispose of the exhausted cell support upon completion of a fermentation.

The reactor used for carrying out the continuous fermentation of this invention is first filled with the solid material used to support the cells of the microorganism. Then sterile medium is added. Finally, the medium is inoculated with a growing culture of the microorganism. The reactor containing the support material, medium and inoculum is incubated for a sufficient time to produce a good growth of cells within the reactor. Such cell growth is indicated by an increased turbidity of the medium.

When cell growth is well established, a continuous fermentation is carried out by passing medium through the reactor. The rate of flow is adjusted to give the desired productivity of acid. Although the direction of medium flow is not critical, upflow through the reactor aids in preventing excess buildup of cell biomass and in promoting flow of the liquid.

The temperature of the reactor during incubation and production of the acid by continuous fermentation is maintained at a temperature between about 45° C. and about 70° C. The pH of the feed medium is maintained between 4.0 and 7.5 by addition of suitable buffer salts to the medium. When the process of this invention is used to prepare acetic acid by fermentation of a carbohydrate with *C. thermoaceticum*, the preferred pH of the feed medium is between about 6.7 and about 7.4 and the preferred temperature is between about 55° C. and about 60° C. The rate of flow of the medium through the reactor is adjusted to give a dilution rate of from about 0.04 to about 3 per hour.

In a satisfactory continuous fermentation, the cells are forming product at a constant rate. When an acid is produced, the steady state condition is indicated by a constant pH. Also, the rate at which new cells are being formed will equal the rate at which cells are being lost from the reactor, giving a constant number of cells within the reactor. Such a steady state condition can be indicated by a constant effluent optical density measured at 540 nm.

In the description of this invention, the words "dilution rate", as used in this application, have the dimensions of per hour expressed as /hr. As pointed out earlier, this rate is obtained by dividing the flow rate of the medium by the total volume of the reactor.

The term "volumetric productivity", as used herein, is determined by multiplying the concentration of the acid in the effluent from the reactor, expressed in grams per liter, by the dilution rate. Units of the volumetric productivity are expressed as g/l-hr.

Acetic acid and glucose concentrations were determined using high-performance liquid chromatography (HPLC). Components were chromatographed by elution with 0.006 N $H_2SO_4$ from a cation-exchange resin in the hydrogen form. Eluted components were detected by means of a differential refractometer, plotted on a recorder and quantitated using an electronic integrator. The area under the curve which represents the concentration of each component is reported as a percentage of the total area. The general procedure is that given in "Analysis of Carbohydrate Mixtures by Liquid Chromatography", *Am. Soc. Brew. Chem. Proc.*, 1973, pp. 43–46. The separations were made on a 1-foot HPX-87 column in the hydrogen form, available from Bio-Rad Laboratories, Richmond, Calif.

The procedure of this invention is further illustrated by the following examples:

EXAMPLE 1

A strain of *C. thermoaceticum*, C5-2, ATCC No. 39,289, was used to produce acetic acid. This acid tolerant strain was obtained by growing the Wood strain, DSM 521, in media at progressively lower pH until it would grow in a medium with a pH below 5.8. It is described in detail in a copending patent application, Ser. No. 474,608, titled "A Mutant Strain of *Clostridium thermoaceticum* Useful for the Preparation of Acetic Acid", filed concurrently with this application, the disclosure of which is incorporated herein by reference in its entirety.

The medium used for growth of the organism had the following composition:

| GROWTH MEDIUM | |
|---|---|
| Component | Concentration (g/liter) |
| A. Glucose | 30.0 |
| B. $NaHCO_3$ | 16.8 |
| $K_2HPO_4$ | 7.0 |
| $KH_2PO_4$ | 5.5 |
| C. Yeast Extract | 5.0 |
| Tryptone | 5.0 |
| $(NH_4)_2SO_4$ | 1.0 |
| $MgSO_4.7H_2O$ | 0.25 |
| $Fe(NH_4)_2(SO_4)_2.6H_2O$ | 0.04 |
| $Co(NO_3)_2.6H_2O$ | 0.03 |
| $NaMoO_4.2H_2O$ | 0.0024 |
| Resazurin (0.20 g/100 ml solution) | 1.0 ml/l |

Solutions of components of Groups A, B, and C were sterilized separately before combining to make a medium of the given composition. Then 0.5 g of sodium thioglycolate, 5.6 mg of nicotinic acid and 1 ml of a trace salt solution were added per liter of medium. The trace salt solution had the following composition:

| TRACE SALT SOLUTION | |
|---|---|
| Component | Concentration (g/liter) |
| Ethylenediaminetetraacetic Acid Disodium Salt Dihydrate | 5.00 |
| $MnCl_2 4H_2O$ | 5.00 |
| $Na_2SeO_3$ | 0.20 |
| $H_3BO_3$ | 0.100 |
| $ZnCl_2$ | 0.050 |
| $AlK(SO_4)_2.12H_2O$ | 0.010 |
| $NiCl_2.6H_2O$ | 0.020 |
| $CuCl_2.2H_2O$ | 0.010 |

Medium preparation and cultivation of samples were carried out using standard anaerobic techniques as described by Hungate, R. E., "A Roll Tube Method for Cultivation of Strict Anaerobes" in *Methods in Microbi-*

*ology*, edited by J. R. Norris and D. W. Ribbons, Vol. 3B, Academic Press, New York, 1969, pp. 117–132, and by Miller and Wolin, *Appl. Microbiol.* 27, 985 (1974). A continuous fermentation was carried out using a culture of *C. thermoaceticum* adsorbed on activated carbon. The degassed fermentation medium was continually passed over a mixture of cells of the microorganism and carbon, held in a jacketed column of 38 ml total volume.

The carrier for the bacterial cells was CPG Pittsburgh activated carbon, 12–40 mesh (U.S. Standard Screen size with sieve openings of 1.68 mm to 0.42 mm), available from the Calgon Corporation, Pittsburgh, Pa. The reactor was filled with 11 g of the carbon, the carbon was moistened with distilled water and the reactor was then sterilized by heating for 2 hours at 121° C. and 15 psi in an autoclave. Sterile anaerobic medium was passed upward through the column to saturate the carbon with the medium. All liquids were held under an atmosphere of carbon dioxide. Approximately 45 bed volumes of medium were passed through the column before it was saturated with all of the medium components.

Inoculum for the carbon bed was prepared by 3 daily sequential subcultures of the strain of *C. thermoaceticum* in medium incubated at 56° C. Then 12 ml of the 3rd subculture which had been incubated for 24 hours was injected into the base of the bed. The column containing the culture was incubated at 58° C. by means of warm water circulating through the jacket of the column. After 12 hours of incubation, turbidity of the medium in the headspace of the column indicated that growth had occurred. Sterile medium was then passed upward through the column at an initial flow rate of 2.5 ml/hr. It was observed that the cells in contact with the support affixed themselves to it, thereby preventing their rapid washout. Optical density (O.D.) at 540 nm, pH, glucose concentration and acetic acid concentration of the effluent were monitored. Flow rate of the medium was varied during the course of the experiment to obtain various dilution rates.

The volumetric productivity at various flow rates is summarized in Table I. The maximum volumetric productivity of 6.0 g/l-hr, observed at a dilution rate of 0.5/hr, was nearly 3 times the best previously-reported volumetric productivity for a fixed-cell reactor with *C. thermoaceticum*. In that process (Wang and Wang), the cells had been fixed in an agar or carrageenan gel.

TABLE I

PRODUCTIVITY OF ACETIC ACID USING ACTIVATED CARBON SUPPORT

| pH | O.D. (540 nm) | Dilution Rate (/hr) | Acetic Acid (g/l) | Volumetric Productivity (g/l hr) |
|---|---|---|---|---|
| 5.25 | 7.4 | 0.09 | 16.9 | 1.5 |
| 5.30 | 3.6 | 0.14 | 16.1 | 2.3 |
| 5.85 | 6.1 | 0.28 | 13.4 | 3.8 |
| 6.40 | 4.2 | 0.50 | 11.9 | 6.0 |

EXAMPLE 2

The general process of Example 1 was followed except that the activated carbon support was replaced with corn cob granules. The corn cob granules used were 14–20 mesh (U.S. Standard Screen size) available from The Anderson's, Maumee, Oh., as Grit-O'Cobs, Grade 1420. The results of the run are given in Table II. When corn cob granules were used as a support for this fixed-cell fermentation, a volumetric productivity of over 14 g/l-hr was obtained at a dilution rate of 2.1/hr. Such a volumetric productivity far exceeds any volumetric productivity previously observed for any homoacidogenic fixed-cell fermentation reaction.

TABLE II

PRODUCTIVITY OF ACETIC ACID USING CORN COB GRANULES SUPPORT

| pH | O.D. (540 nm) | Dilution Rate (/hr) | Acetic Acid (g/l) | Volumetric Productivity (g/l hr) |
|---|---|---|---|---|
| 5.6 | 4.2 | 0.29 | 13.4 | 3.9 |
| 6.0 | 3.8 | 0.74 | 10.2 | 7.5 |
| 5.9 | 3.9 | 0.75 | 10.4 | 7.8 |
| 6.4 | 3.5 | 1.2 | 10.2 | 12.2 |
| 6.9 | 2.8 | 2.1 | 7.1 | 14.3 |

COMPARATIVE TEST 1

For comparison purposes, a continuous fermentation was carried out in a stirred reactor which contained only medium and cells with no other solid material to act as a support. The fermentation was conducted at 58° C. and the flow rates were varied during the course of the experiment as in Example 1. The maximum volumetric productivity of 1.76 g/l-hr was observed at a dilution rate of 0.23/hr. Dilution rates above about 0.3 are not possible in such a system since the cells wash out of the reactor at higher dilution rates. Results of the tests, given in Table III, show that a process using a continuous reactor without cell support gives much lower volumetric productivity than does the process of the present invention.

TABLE III

PRODUCTIVITY OF ACETIC ACID USING A STIRRED REACTOR WITH NO CELL SUPPORT

| pH | O.D. (540 nm) | Dilution Rate (/hr) | Acetic Acid (g/l) | Volumetric Productivity (g/l hr) |
|---|---|---|---|---|
| 6.7 | 7.4 | 0.20 | 8.2 | 1.66 |
| 6.8 | 7.0 | 0.23 | 7.6 | 1.76 |
| 7.0 | 3.4 | 0.30 | 4.9 | 1.50 |

COMPARATIVE TEST 2

The general process of Example 1 was followed except that the activated carbon support was replaced with reticulated polyurethane foam cut to fit in the column. The foam used was Scott Filter Foam containing 20 pores per linear inch. It is available from the Scott Paper Company, Foam Division, Chester, Pa. The results of the run are given in Table IV. When *C. thermoaceticum* cells are adsorbed on this support, they give considerably lower volumetric productivity of acetic acid than when they are adsorbed on the supports used in the process of the present invention.

TABLE IV

PRODUCTIVITY OF ACETIC ACID USING RETICULATED POLYURETHANE FOAM SUPPORT

| pH | O.D. (540 nm) | Dilution Rate (/hr) | Acetic Acid (g/l) | Volumetric Productivity (g/l hr) |
|---|---|---|---|---|
| 5.8 | 4.9 | 0.12 | 13.3 | 1.6 |
| 6.4 | 5.4 | 0.28 | 10.1 | 2.8 |
| 6.9 | 2.5 | 0.96 | 4.4 | 4.2 |
| 7.0 | 2.4 | 1.0 | 3.9 | 3.9 |
| 7.0 | 2.3 | 1.1 | 3.4 | 3.7 |
| 7.2 | 1.4 | 1.9 | 1.8 | 3.4 |

Thus, it is apparent that there has been provided, in accordance with the invention, an improved process for the continuous production of an organic acid by a homoacidogenic reaction which is superior to the processes of the prior art. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A process for the continuous production of an organic acid by a homoacidogenic fermentation reaction characterized in that the acid is produced by fermenting a carbohydrate solution by passing the solution over cells of a homoacidogenic microorganism growing on the surface of a support material selected from the group consisting of activated carbon or corn cob granules under conditions of pH, temperature and dilution rate effective to produce the acid at a volumetric productivity of at least about 5 g/1-hr.

2. The process of claim 1 wherein the homoacidogenic microorganism is a strain of *C. thermoaceticum* and the acid is acetic acid.

3. The process of claim 2 wherein the strain of *C. thermoaceticum* is ATCC No. 39,289.

4. The process of claim 3 wherein the carbohydrate solution is an aqueous solution of glucose.

5. The process of claim 3 wherein the pH is held between about 4.0 and about 7.5.

6. The process of claim 3 wherein the temperature is held between about 45° C. and about 70° C.

7. The process of claim 3 wherein the dilution rate is between about 0.4/hr and about 3/hr.

8. The process of claim 4 wherein the pH is held between about 4.0 and about 7.5.

9. The process of claim 4 wherein the temperature is held between about 45° C. and about 70° C.

10. The process of claim 4 wherein the dilution rate is between about 0.4/hr and about 3/hr.

11. The process of claim 1 wherein the carbohydrate solution is passed through a degassing chamber before it is passed over the cells of the microorganism.

12. The process of claim 1 wherein the homoacidogenic microorganism is a strain of *Lactobacillus delbrueckii* and the acid is lactic acid.

* * * * *

UNITED STATES PATENT AND TRADEMARK OFFICE
CERTIFICATE OF CORRECTION

PATENT NO. : 4,506,012
DATED : March 19, 1985
INVENTOR(S) : William M. Reed

It is certified that error appears in the above-identified patent and that said Letters Patent are hereby corrected as shown below:

Column 1, line 43, "yeilds" should read --yields--.

Column 4, line 61, "0.010" should read --0.100--.

Signed and Sealed this

Eighth Day of October 1985

[SEAL]

Attest:

DONALD J. QUIGG

Attesting Officer

Commissioner of Patents and
Trademarks—Designate